(12) United States Patent
Pinsonneault

(10) Patent No.: US 8,386,274 B1
(45) Date of Patent: Feb. 26, 2013

(54) SYSTEMS AND METHODS FOR A PRESCRIPTION SAFETY NETWORK UTILIZING ELIGIBILITY VERIFICATION TRANSACTIONS

(75) Inventor: Roger Pinsonneault, Alpharetta, GA (US)

(73) Assignee: McKesson Financial Holdings Limited (BM)

( * ) Notice: Subject to any disclaimer, the term of this patent is extended or adjusted under 35 U.S.C. 154(b) by 486 days.

(21) Appl. No.: 12/212,129

(22) Filed: Sep. 17, 2008

(51) Int. Cl.
*G06Q 50/00* (2012.01)
(52) U.S. Cl. .......................................... 705/2
(58) Field of Classification Search ............... 705/2–4; 600/300–301
See application file for complete search history.

(56) References Cited

U.S. PATENT DOCUMENTS

| | | | |
|---|---|---|---|
| 5,628,530 A | 5/1997 | Thornton | |
| 5,970,472 A * | 10/1999 | Allsop et al. ............... | 705/26.81 |
| 6,012,035 A | 1/2000 | Freeman et al. | |
| 6,045,501 A | 4/2000 | Elsayed et al. | |
| 6,055,507 A | 4/2000 | Cunningham | |
| 6,315,720 B1 | 11/2001 | Williams et al. | |
| 6,561,976 B2 | 5/2003 | Elsayed et al. | |
| 6,561,977 B2 | 5/2003 | Williams et al. | |
| 6,602,469 B1 * | 8/2003 | Maus et al. ................... | 422/68.1 |
| 6,757,898 B1 | 6/2004 | Ilsen et al. | |
| 6,769,228 B1 | 8/2004 | Mahar | |
| 6,952,681 B2 | 10/2005 | McQuade et al. | |
| 6,994,249 B2 | 2/2006 | Peterka et al. | |
| 7,040,856 B2 | 5/2006 | Reich | |
| 7,086,133 B2 | 8/2006 | Reich | |
| 7,096,072 B2 | 8/2006 | Engleson et al. | |
| 7,103,419 B2 | 9/2006 | Engleson et al. | |
| 7,107,106 B2 | 9/2006 | Engleson et al. | |
| 7,117,041 B2 | 10/2006 | Engleson et al. | |
| 7,155,397 B2 | 12/2006 | Alexander et al. | |

(Continued)

FOREIGN PATENT DOCUMENTS

| CA | 2482370 | 3/2006 |
|---|---|---|
| WO | 9503569 | 2/1995 |

(Continued)

OTHER PUBLICATIONS

Sampson, R.J., Taking Control of Health Care Costs, Best's Review—Life Health Insurance Edition, Nov. 1983, pp. 64-66, vol. 84, Issue 7, USA.

(Continued)

*Primary Examiner* — John Pauls
(74) *Attorney, Agent, or Firm* — Sutherland Asbill & Brennan LLP

(57) ABSTRACT

Systems and methods may be provided for a prescription safety network program. The systems and methods may include receiving an eligibility verification request for a prescribed drug or product, where the eligibility verification request may include a pharmacy identifier, a patient identifier, and physician identifier; determining, based upon the received pharmacy identifier, that a pharmacy associated with the pharmacy identifier has enrolled in the prescription safety network program for filling the prescribed drug or product; determining, based upon the received patient identifier, that a patient associated with the patient identifier has enrolled in the prescription safety network program for utilizing the prescribed drug or product; and determining, based upon the received physician identifier, that a physician associated with the physician identifier has enrolled in the prescription safety network program for prescribing the prescribed drug or product; and generating an approval authorization by the validation engine in response to the eligibility verification request.

20 Claims, 9 Drawing Sheets

U.S. PATENT DOCUMENTS

| | | | |
|---|---|---|---|
| 7,171,277 | B2 | 1/2007 | Engleson et al. |
| 7,175,081 | B2 | 2/2007 | Andreasson et al. |
| 7,469,213 | B1 | 12/2008 | Rao |
| 7,483,756 | B2 | 1/2009 | Engleson et al. |
| 7,668,730 | B2 | 2/2010 | Reardan et al. |
| 7,739,127 | B1 * | 6/2010 | Hall ................................. 705/2 |
| 7,765,106 | B2 | 7/2010 | Reardan et al. |
| 7,765,107 | B2 * | 7/2010 | Reardan et al. ................... 705/2 |
| 7,813,938 | B2 | 10/2010 | Kusterbeck |
| 7,885,824 | B1 | 2/2011 | Koneru |
| 7,895,059 | B2 | 2/2011 | Reardan et al. |
| 7,976,508 | B2 | 7/2011 | Hoag |
| 8,036,911 | B2 | 10/2011 | Bellon et al. |
| 8,112,290 | B2 | 2/2012 | Maurer et al. |
| 2002/0002495 | A1 | 1/2002 | Ullman |
| 2002/0087583 | A1 | 7/2002 | Morgan et al. |
| 2002/0111828 | A1 | 8/2002 | Bloder et al. |
| 2002/0111832 | A1 | 8/2002 | Judge |
| 2002/0198831 | A1 | 12/2002 | Patricelli et al. |
| 2003/0009367 | A1 | 1/2003 | Morrison |
| 2003/0050799 | A1 | 3/2003 | Jay et al. |
| 2003/0055683 | A1 * | 3/2003 | Gibson et al. ...................... 705/2 |
| 2003/0149625 | A1 | 8/2003 | Leonardi et al. |
| 2003/0154163 | A1 | 8/2003 | Phillips et al. |
| 2003/0229540 | A1 | 12/2003 | Algiene |
| 2004/0019794 | A1 * | 1/2004 | Moradi et al. ................ 713/185 |
| 2004/0039599 | A1 | 2/2004 | Fralic |
| 2004/0073457 | A1 | 4/2004 | Kalies |
| 2004/0078234 | A1 | 4/2004 | Tallal, Jr. |
| 2004/0117323 | A1 | 6/2004 | Mindala |
| 2004/0148198 | A1 | 7/2004 | Kalies |
| 2004/0249745 | A1 | 12/2004 | Baaren |
| 2005/0015280 | A1 | 1/2005 | Gabel et al. |
| 2005/0060201 | A1 | 3/2005 | Connely et al. |
| 2005/0102169 | A1 | 5/2005 | Wilson |
| 2005/0154627 | A1 | 7/2005 | Zuzek et al. |
| 2005/0187793 | A1 | 8/2005 | Myles |
| 2005/0197862 | A1 | 9/2005 | Paterson et al. |
| 2005/0240473 | A1 | 10/2005 | Ayers |
| 2005/0288972 | A1 | 12/2005 | Marvin et al. |
| 2006/0020514 | A1 | 1/2006 | Yered |
| 2006/0026041 | A1 | 2/2006 | Ullman et al. |
| 2006/0054682 | A1 * | 3/2006 | de la Huerga ................ 235/375 |
| 2006/0149784 | A1 | 7/2006 | Tholl et al. |
| 2006/0184391 | A1 | 8/2006 | Barre et al. |
| 2006/0259363 | A1 | 11/2006 | Jhetam |
| 2007/0005402 | A1 | 1/2007 | Kennedy et al. |
| 2007/0043586 | A1 | 2/2007 | Arellano |
| 2007/0050209 | A1 | 3/2007 | Yered |
| 2007/0088461 | A1 | 4/2007 | Haitin et al. |
| 2007/0136100 | A1 | 6/2007 | Daugherty et al. |
| 2007/0233525 | A1 | 10/2007 | Boyle |
| 2007/0233526 | A1 | 10/2007 | Hoffman et al. |
| 2007/0239493 | A1 * | 10/2007 | Sweetland et al. ................. 705/4 |
| 2007/0260491 | A1 | 11/2007 | Palmer et al. |
| 2008/0201173 | A1 * | 8/2008 | Takehara et al. ................... 705/3 |
| 2008/0306796 | A1 | 12/2008 | Zimmerman et al. |
| 2009/0094051 | A1 | 4/2009 | Ard et al. |
| 2009/0125326 | A1 * | 5/2009 | Wasson et al. .................... 705/2 |
| 2009/0246265 | A1 | 10/2009 | Stinchcomb et al. |
| 2010/0057489 | A1 | 3/2010 | Howe et al. |
| 2010/0082458 | A1 | 4/2010 | Godlewski |
| 2010/0256984 | A1 | 10/2010 | Gold et al. |
| 2010/0287002 | A1 | 11/2010 | Barre et al. |
| 2011/0010328 | A1 | 1/2011 | Patel et al. |
| 2011/0106556 | A1 | 5/2011 | Patel et al. |
| 2011/0119085 | A1 | 5/2011 | Reardan et al. |
| 2011/0145018 | A1 | 6/2011 | Fotsch et al. |
| 2011/0182807 | A1 | 7/2011 | Fuisz et al. |
| 2011/0184747 | A1 | 7/2011 | Bozic et al. |
| 2011/0184753 | A1 | 7/2011 | Tripoli |
| 2011/0184755 | A1 | 7/2011 | Yamaga et al. |
| 2011/0184756 | A1 | 7/2011 | Yamaga et al. |
| 2011/0209065 | A1 | 8/2011 | Del Rio et al. |

FOREIGN PATENT DOCUMENTS

| | | |
|---|---|---|
| WO | 0039737 | 7/2000 |
| WO | 2007025295 | 3/2007 |

OTHER PUBLICATIONS

Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.

Lamb, J., New Era of Electronic Medicine Management: E-Prescriptions, Britain's Traditionally Cautious National Health Service is Starting Trials for Online Prescription, with the Aim of Cutting Costs. Financial Times, London, Feb. 21, 2001, p. 6, London, United Kingdom.

Anonymous, Pharmacy Industry Leaders Launch Firm to Supply Real-Time Data. PR Newswire. Jul. 30, 2001, p. 1, New York, NY, USA.

Anonymous, Medic: On-line Goes In-House, Chain Store Age Executive, Jan. 1987, pp. 128-132. vol. 63, Issue 1, USA.

Anonymous, TechRx Announces Successful Beta Deployment of T-Rex. PR Newswire. May 13, 2002.

Non-Final Office Action for U.S. Appl. No. 12/468,102 mailed May 27, 2011.

Final Office Action for U.S. Appl. No. 12/468,102 mailed Nov. 16, 2011.

Non-Final Office Action for U.S. Appl. No. 12/552,825 mailed Dec. 2, 2011.

Non-Final Office Action for U.S. Appl. No. 12/776,974 mailed Jan. 3, 2012.

Federal Register—vol. 77, No. 39; Tuesday, Feb. 28, 2012; Notices (pp. 12059-12062).

Final Office Action for U.S. Appl. No. 12/552,825 mailed May 1, 2012.

Final Office Action for U.S. Appl. No. 12/776,974 mailed May 25, 2012.

Notice of Allowance for U.S. Appl. No. 12/776,974 mailed Nov. 29, 2012.

* cited by examiner

Prescription Safety Network

Prescription Authorizations

Pharmacist: Identify "Pharmacy NPI", "Rx Patient ID", "Prescriber NPI". Press <Submit> and await authorization from the PRESCRIPTION SAFETY NETWORK. Questions? Call (800) XXX-XXXX > PRESCRIPTION SAFETY NETWORK
> REQUEST DENIED
> PATIENT NOT REGISTERED
> CONTACT (800) XXX-XXXX

< EXIT >

FIG. 6A

Prescription Safety Network

Prescription Authorizations

Pharmacist: Identify "Pharmacy NPI", "Rx Patient ID", "Prescriber NPI". Press <Submit> and await authorization from the PRESCRIPTION SAFETY NETWORK. Questions? Call (800) XXX-XXXX

```
PRESCRIPTION SAFETY NETWORK
REQUEST APPROVED!
AUTHORIZATION ID – A123456
DELIVER MEDICATION GUIDE TO
PATIENT
& VERIFY PRESCRIPTION DOSING
```

< EXIT >

FIG. 6B

SYSTEMS AND METHODS FOR A PRESCRIPTION SAFETY NETWORK UTILIZING ELIGIBILITY VERIFICATION TRANSACTIONS

FIELD OF THE INVENTION

Aspects of the invention relate generally to prescription drugs or products, and more particularly, to systems and methods for enforcing optimal medication prescribing and/or usage through a prescription safety network.

BACKGROUND OF THE INVENTION

The U.S. Food & Drug Administration (FDA) has provided industry guidance on Risk Management, including the development and use of Risk Minimization Action Plans (Risk-MAPS) and Risk Evaluation and Mitigation Strategy (REMS). Specifically, risk management is an iterative process of (1) assessing a product's benefit-risk balance, (2) developing and implementing tools to minimize its risks while preserving its benefits, (3) evaluating tool effectiveness and reassessing the benefit-risk balance, and (4) making adjustments, as appropriate, to the risk minimization tools to further improve the benefit-risk balance. Accordingly, there is a need in the industry for systems and methods for supporting Risk Management of prescribed drugs or other products.

SUMMARY OF THE INVENTION

According to an example embodiment of the invention, there may be a method for a prescription safety network program. The method may include receiving, by a validation engine associated with the prescription safety network program, an eligibility verification request for a prescribed drug or product, where the eligibility verification request includes a pharmacy identifier, a patient identifier, and physician identifier; determining, by the validation engine based upon the received pharmacy identifier, that a pharmacy associated with the pharmacy identifier has enrolled in the prescription safety network program for filling the prescribed drug or product; determining, by the validation engine based upon the received patient identifier, that a patient associated with the patient identifier has enrolled in the prescription safety network program for utilizing the prescribed drug or product; and determining, by the validation engine based upon the received physician identifier, that a physician associated with the physician identifier has enrolled in the prescription safety network program for prescribing the prescribed drug or product; and generating an approval authorization by the validation engine in response to the eligibility verification request, wherein the approval authorization permits the pharmacy to provide the prescribed drug or product to the patient.

According to another example embodiment of the invention, there may be a system for a prescription safety network program. The system may include a memory for storing computer-executable instructions, and a processor in communication with the memory. The processor may be configured to execute the computer-executable instructions to receive an eligibility verification request for a prescribed drug or product, where the eligibility verification request includes a pharmacy identifier, a patient identifier, and physician identifier; determine, based upon the received pharmacy identifier, that a pharmacy associated with the pharmacy identifier has enrolled in a prescription safety network program for filling the prescribed drug or product; determine, based upon the received patient identifier, that a patient associated with the patient identifier has enrolled in the prescription safety network program for utilizing the prescribed drug or product; determine, based upon the received physician identifier, that a physician associated with the physician identifier has enrolled in the prescription safety network program for prescribing the prescribed drug or product; and generate an approval authorization by the validation engine in response to the eligibility verification request, wherein the approval authorization permits the pharmacy to provide the prescribed drug or product to the patient.

BRIEF DESCRIPTION OF THE DRAWINGS

Reference will now be made to the accompanying drawings, which are not necessarily drawn to scale, and wherein:

FIG. 6A illustrates an example message for an authorization denial, according to an example embodiment of the invention.

FIG. 6B illustrates an example message for an authorization approval, according to an example embodiment of the invention.

DETAILED DESCRIPTION

Figure 1:
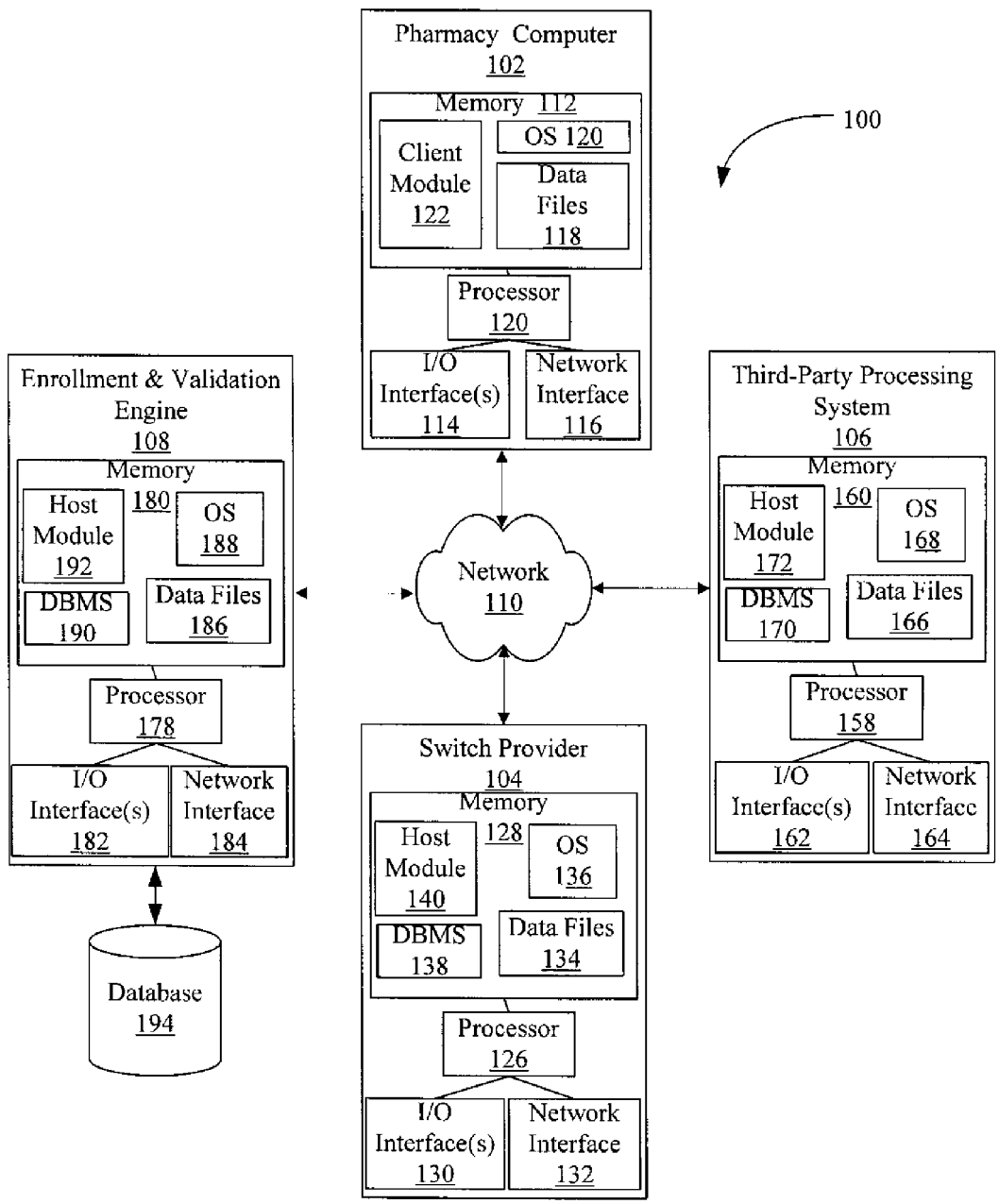
FIG. 1 illustrates an example system for implementing a Prescription Safety Network program in accordance with an embodiment of the invention.

Example embodiments of invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Embodiments of the invention may be described below with reference to block diagrams and flowchart illustrations of systems, methods, apparatuses and computer program products according to embodiments of the invention. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, processor, or other programmable data processing apparatus to produce a machine, such that the instructions which execute on the computer or other programmable data processing apparatus create means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including instruction means that implement the function specified in the flowchart block or blocks. The computer program instructions may also be loaded onto a computer or other programmable data processing apparatus to cause a series of operational elements or steps to be performed on the computer or other programmable apparatus to produce a computer implemented process such that the instructions that execute on the computer or other programmable apparatus provide elements or steps for implementing the functions specified in the flowchart block or blocks.

Accordingly, blocks of the block diagrams and flowchart illustrations support combinations of means for performing the specified functions, combinations of elements or steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions, elements or steps, or combinations of special purpose hardware and computer instructions.

Example embodiments of the invention may be directed towards systems and methods for registering or enrolling physicians or other healthcare providers (e.g., physician's representative, nurse practitioner, physician assistant, etc.), pharmacies/pharmacists, and/or patients/caregivers in a Prescription Safety Network program. A Prescription Safety Network program may be utilized by a pharmaceutical manufacturer as part of a Risk Minimization Action Plan (Risk-MAP) or Risk Evaluation and Mitigation Strategy (REMS) in accordance with U.S. Food and Drug Administration (FDA) guidelines. The registered or enrolled physicians or other healthcare providers, pharmacies/pharmacists, and/or patients/caregivers may receive educational or training information regarding one or more drugs or other products (e.g., medical devices), including medication safety guidelines or usage information. The registration or enrollment information may be stored for subsequent use in determining whether to provide authorization for filling or refilling a prescription.

An example system for implementing a Prescription Safety Network program in accordance with an embodiment of the invention is shown in FIG. 1. As shown in FIG. 1, the system 100 may include a pharmacy computer 102, a switch provider 104, a third-party processing system 106, and an enrollment & validation engine 108, which are each configured for accessing and reading associated computer-readable media having stored thereon data and/or computer-executable instructions for implementing the various methods of the invention. Generally, network devices and systems, including the one or more pharmacy computers 102, switch providers 104, third-party processing systems 106, and enrollment & validation engines 108 have hardware and/or software for transmitting and receiving data and/or computer-executable instructions over a communications link and a memory for storing data and/or computer-executable instructions. These network devices and systems may also include a processor for processing data and executing computer-executable instructions, as well as other internal and peripheral components that are well known in the art. As used herein, the term "computer-readable medium" describes any form of memory or a propagated signal transmission medium. Propagated signals representing data and computer-executable instructions are transferred between network devices and systems.

As shown in FIG. 1, the pharmacy computer 102, switch provider 104, third-party processing system 106, and the enrollment & validation engine 108 may be in communication with each other via a network 110, which as described below can include one or more separate or shared private and public networks, including the Internet. Each of these components—the pharmacy computer 102, switch provider 104, third-party processing system 106, enrollment & validation engine 108, and the network 110—will now be discussed in further detail.

First, the pharmacy computer 102 may be any processor-driven device, such as a personal computer, laptop computer, handheld computer, and the like. In addition to having a processor 119, the pharmacy computer 102 may further include a memory 112, input/output ("I/O") interface(s) 114, and a network interface 116. The memory 112 may store data files 118 and various program modules, such as an operating system ("OS") 120 and a client module 122. The client module 122 may be an Internet browser or other software, including a dedicated program, for interacting with the switch provider 104, the third-party processing system 106, and/or enrollment & validation engine 108. For example, a user such as a pharmacist or other pharmacy employee may utilize the client module 122 in preparing and providing an eligibility verification request or prescription claim request to the switch provider 104 for processing and/or routing. The pharmacy computer 102 may also utilize the client module 122 to retrieve or otherwise receive data from the switch provider 104. Additionally, the pharmacist or pharmacy employee may also use the client module 122 to enroll with and receive educational content from the enrollment & validation engine 108. Still referring to the pharmacy computer 102, the I/O interface(s) 114 may facilitate communication between the processor 120 and various I/O devices, such as a keyboard, mouse, printer, microphone, speaker, monitor, bar code readers/scanners, RFID readers, and the like. The network interface 116 may take any of a number of forms, such as a network interface card, a modem, a wireless network card, and the like.

The switch provider 104 may include any processor-driven device that is configured for receiving, processing, and fulfilling requests from the pharmacy computer 102, third-party processing system 106, and/or enrollment & validation engine 108 relating to enrollment, eligibility verification, and prescription claim transactions. The switch provider 104 may include a processor 126, a memory 128, input/output ("I/O") interface(s) 130, and a network interface 132. The memory 128 may store data files 134 and various program modules, such as an operating system ("OS") 136, a database management system ("DBMS") 138, and the host module 140. The host module 140 receives, processes, and responds to requests from the client module 122 of pharmacy computer 102, and further receives, processes, and responds to requests from the host module 172 of the third-party processing system 106. Likewise, where the enrollment & validation engine 108 is provided separately from the switch provider 104, the host module 140 may route eligibility verification requests to the enrollment & validation engine 108 for validations, as described herein.

The third-party processing system 106 may be a claims processor, according to an example embodiment of the invention. The third-party processing system 106 may include a processor 158, a memory 160, input/output ("I/O") interface(s) 162, and a network interface 164. The memory 160 may store data files 166 and various program modules, such as an operating system ("OS") 168, a database management system ("DBMS") 170, and a host module 172. The host module 172 may receive, process, and respond to requests from the client module 122 of pharmacy computer 102, and may further receive, process, and respond to requests from the host module 140 of the switch provider 104. According to an example embodiment of the invention, the third-party processing system 106 may be associated with benefits determination by a discount processor, an insurance company, a pharmacy benefits manger (PBM), and the like.

The enrollment & validation engine 108 may include a processor-driven device that is configured for enrolling or otherwise qualifying physicians or other healthcare providers, pharmacies/pharmacists, and/or patients/caregivers for prescribing, dispensing, and/or using one or more prescribed or regulated drugs. For example, registration or enrollment may occur by a physician, pharmacy, pharmacist, and/or patient/caregiver accessing the enrollment & validation engine 108 via a call center or interactive voice response (IVR) system that communicates with the enrollment & validation engine 108. Alternatively, enrollment may also occur by a physician, pharmacy, pharmacist, and/or patient/caregiver accessing the enrollment & validation engine 108 via a network or Internet portal/website. Additionally, the enrollment & validation engine 108 may include one or more business rules for validating eligibility verification requests associated with filling and refilling prescriptions for one or more drugs. It will be appreciated that while the enrollment & validation engine 108 has been illustrated in FIG. 1 as a single processor-driven device, the engine 108 may also be two or more distinct processor-driven devices for performing the respective enrollments and validations, according to an example embodiment of the invention.

The enrollment & validation engine 108 may include a processor 178, a memory 180, input/output ("I/O") interface(s) 182, and a network interface 184. The memory 180 may store data files 186 and various program modules, such as an operating system ("OS") 188, a database management system ("DBMS") 190, and a host module 192. The host module 192 may receive, process, and respond to requests relating to registration or enrollment by a physician or other healthcare provider, pharmacy/pharmacist, and patient/caregiver. The host module 192 may also receive, process, and respond to eligibility verification requests associated with filling or refilling prescriptions for one or more drugs, according to an example embodiment of the invention. Information associated with the enrollment and/or validation may be stored in a database 194. The database 194 may include one or more registries for storing registration or enrollment information for the physician or other healthcare provider, pharmacy/pharmacist, and/or patient/caregiver. The database 194 can also include informational or educational content related to a prescription drug or product. Likewise, the database 194 may include records relating to validations (e.g., date/time, approved, denied) of eligibility verification requests associated with filling and refilling prescriptions for one or more drugs.

The network 110 may include any telecommunication and/or data network, whether public, private, or a combination thereof, including a local area network, a wide area network, an intranet, an internet, the Internet, intermediate hand-held data transfer devices, a publicly switched telephone network (PSTN), and/or any combination thereof and may be wired and/or wireless. The network 110 may also allow for real-time, off-line, and/or batch transactions to be transmitted between the pharmacy computer 102 and the switch provider 104. Due to network connectivity, various methodologies as described herein may be practiced in the context of distributed computing environments. It will also be appreciated that the network 110 may include a plurality of networks, each with devices such as gateways and routers for providing connectivity between or among networks 110. Instead of or in addition to a network 110, dedicated communication links may be used to connect the various devices in accordance with example embodiment invention. For example, the switch provider 104 may form the basis of network 110 that interconnects the pharmacy computer 102 and the third-party processing system 106.

Those of ordinary skill in the art will appreciate that the system 100 shown in and described with respect to FIG. 1 is provided by way of example only. Numerous other operating environments, system architectures, and device configurations are possible. Accordingly, embodiments of the invention should not be construed as being limited to any particular operating environment, system architecture, or device configuration.

Figure 2:
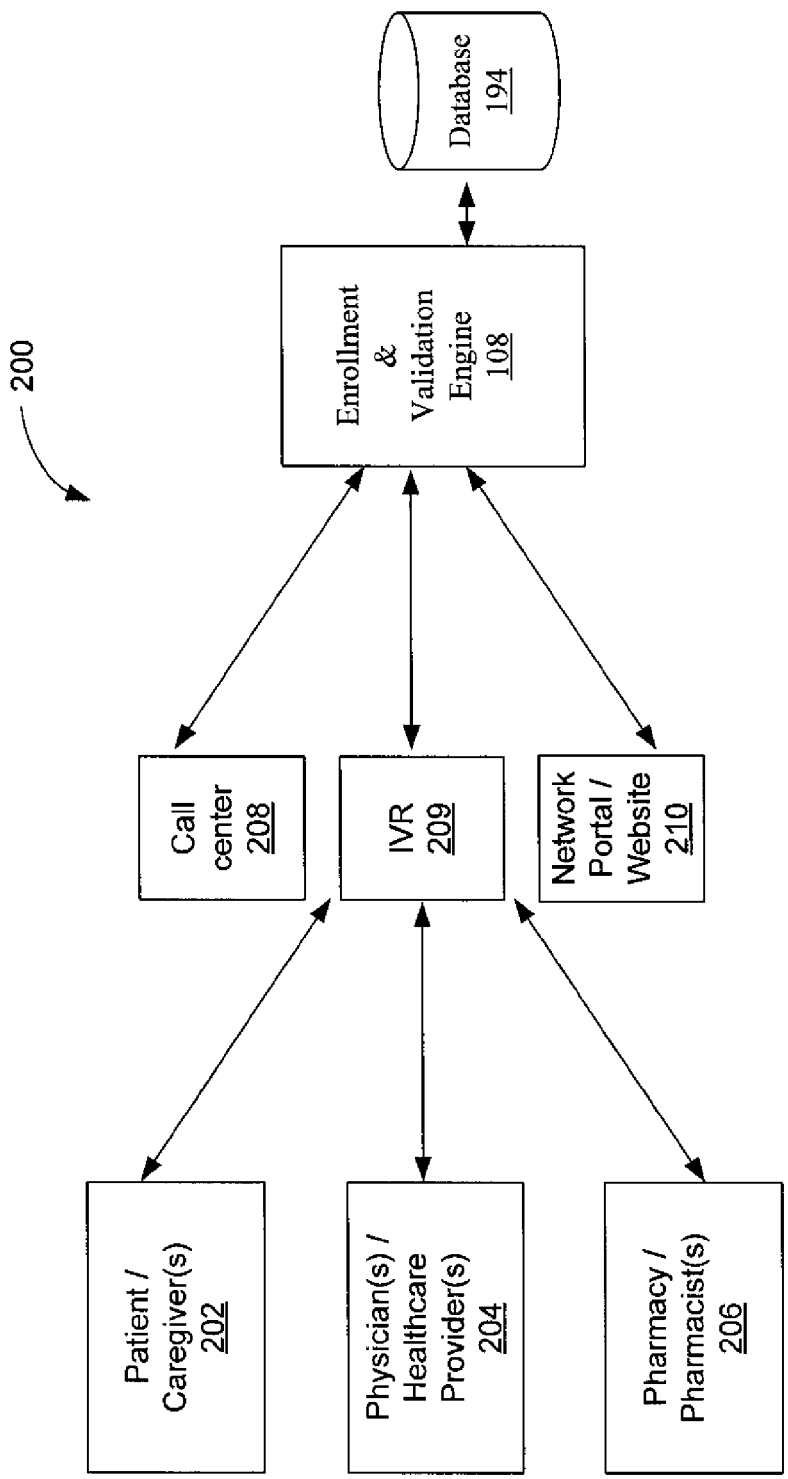
FIG. 2 illustrates an example block diagram for registration or enrollment of one or more patient/caregivers, physicians/healthcare providers, and/or pharmacies/pharmacists with a Prescription Safety Network program, according to an example embodiment of the invention.

FIG. 2 illustrates an example block diagram for registration or enrollment of one or more patient/caregivers 202, physicians/healthcare providers 204, and/or pharmacies/pharmacists 206 with a Prescription Safety Network program administered or sponsored by an enrollment & validation engine 108. As shown in FIG. 2, the patient/caregiver 202, physician/healthcare provider 204, and/or pharmacy/pharmacist 206 may enroll in a Prescription Safety Network program by communicating with enrollment & validation engine 108 via a call center 208, an interactive voice response (IVR) system 208, or a network portal/website 210. The operation of the block diagram of FIG. 2 will be discussed in conjunction with the flow diagram of FIG. 3.

Figure 3:
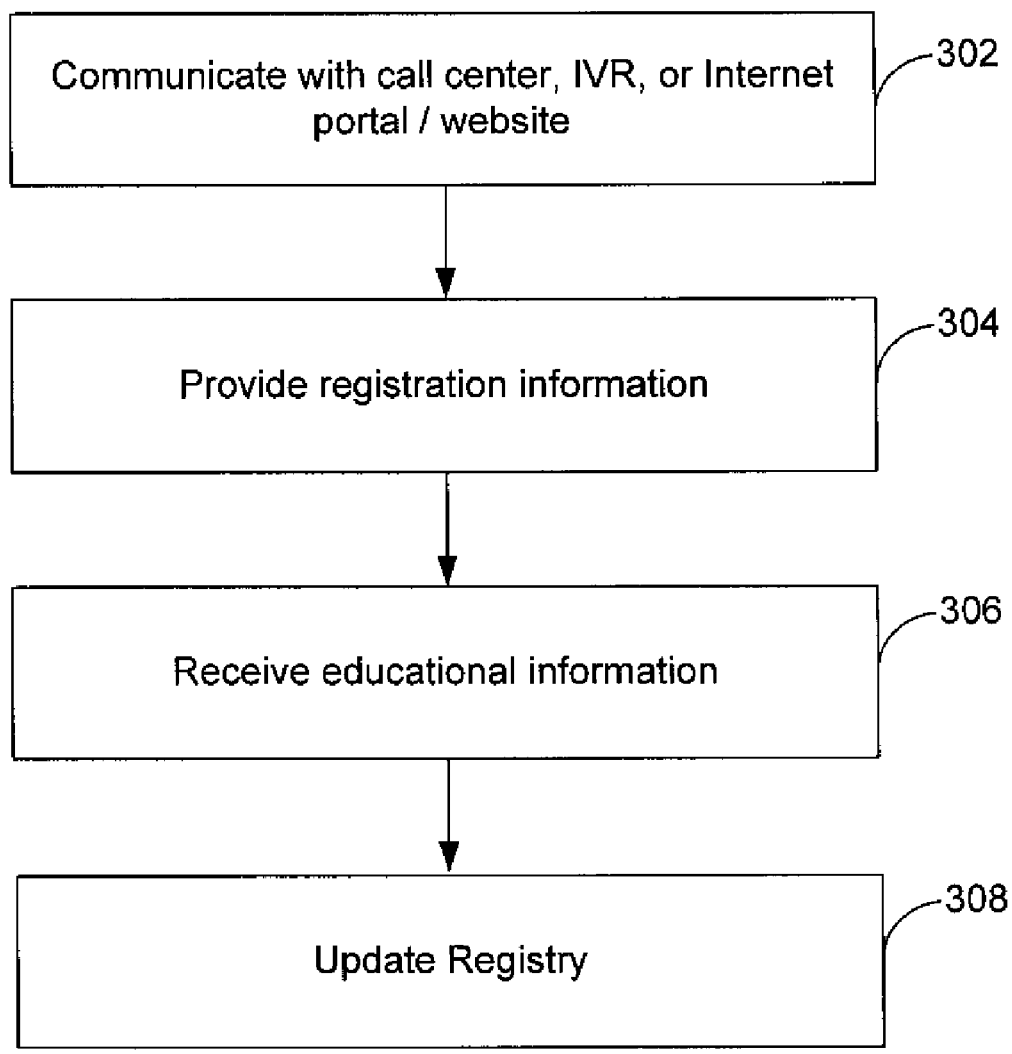
FIG. 3 illustrates an example flow diagram for registration or enrollment in a Prescription Safety Network program for one or more prescription drugs, according to an example embodiment of the invention.

FIG. 3 illustrates a flow diagram for registration or enrollment in a Prescription Safety Network program for one or more prescription drugs, according to an example embodiment of the invention. The registration or enrollment may be necessary for a patient/caregiver 202, physician/healthcare provider 204, and/or pharmacy/pharmacist 206 to use, prescribe, and/or dispense a particular prescription drug or product, according to an example embodiment of the invention. As shown in block 302, patient/caregiver 202, physician/healthcare provider 204, and/or pharmacy/pharmacist 206 may use a telephone to contact a call center 208 or IVR system 209 in enrolling with the enrollment & validation engine 108. The call center 208 may be staffed with a customer service representative while the IVR system 209 may be responsive to touch-tone telephone inputs. The IVR system 209 may also be capable of transcribing or recognizing received verbal inputs. Alternatively, the patient/caregiver 202, physician/healthcare provider 204, and/or pharmacy/pharmacist 206 may use a computer (e.g., pharmacy computer 102 or another similar computer) to communicate with a network portal/website 210. The network portal/website 210 may be an Internet-based portal or website, according to an example embodiment of the invention.

Still referring to FIG. 3, in block 304, the patient/caregiver 202, physician/healthcare provider 204, and/or pharmacy/pharmacist 206 may provide the call center 208 and/or network portal/website 210 with enrollment information. For a patient/caregiver 202, the enrollment information in block 304 may include one or more of the following:

identification information for the patient/caregiver 202 (e.g., a name, social security number, etc.);

contact information such as an address, telephone number, fax number, email address, etc.;

a identification of at least one drug or product that may be prescribed for the patient;

demographic information associated with the patient such as sex, weight, date of birth (DOB); and/or medical information associated with the patient such as current ailments, conditions, medications, or any other information that may be used to determine the appropriate of a proposed drug or product or continued receipt of an existing drug or product.

In addition to receiving the enrollment information, block 304 may also include verifying that the patient meets certain requirements (e.g., age, weight, etc.) to utilize the drug or product, including validating the patient's tolerance for the drug or product.

For a physician/healthcare provider 204, the enrollment information in block 304 may include one or more of the following:

identification information such as a name;

contact information, such as an address, telephone number, fax number, email address, etc.;

a physician/healthcare provider identifier, such as a DEA #, NPI (National Provider Identifier), State License number, or the like;

an identification of a physician's/healthcare provider's specialty (for optional use in determining qualifications of a physician/healthcare provider); and/or identification of at least one drug or product that may be prescribed by the physician/healthcare provider 204.

Similarly, for the pharmacy/pharmacist(s) 206, the enrollment information in block 304 may include one or more of the following:

identification information such as a name for the pharmacy or pharmacist(s) at the pharmacy;

contact information, such as an address, telephone number, fax number, email address, etc.;

an identification of at least one drug or product that may be prescribed (or at least one disease or condition that may be handled);

a pharmacy identification number, such as a DEA (Drug Enforcement Agency) number, NPI (National Provider Identifier), NCPDP Provider ID, or State License #; and/or identification of any special pharmacy training that may uniquely qualify the pharmacy/pharmacist to qualify for program participation.

It will be appreciated that block 304 may likewise involve the enrollment & validation engine 108 or another entity verifying that the received information is acceptable and/or in the proper format. This verification may ensure that the stored information in database 194 is operable for subsequent use by the enrollment & validation engine 108.

In block 306, the enrolling patient/caregiver 202, physician/healthcare provider 204, and/or pharmacy/pharmacist 206 may receive educational or training information associated with the prescription drug or product (or alternatively, a certain disease or condition). For example, the educational or training information may be verbally provided by the call center 208, either through the customer service representative or the IVR system. Likewise, for the network portal/website 210 may provide the educational or training information on the portal/website 210. According to an example embodiment of the invention, however, the educational or training information may also be provided by facsimile, email, postal mail, in-person, and the like. By way of example, the educational or training information delivered to a patient/caregiver 202 may include an education and risk management tutorial, usage instructions for the drug or product, and/or a medication or safety guide for using the drug or product, according to an example embodiment of the invention. Likewise, for a physician/healthcare provider 204 may be provided with a an education and risk management tutorial or other training program for prescribing the drug or product. Similarly, the pharmacy/pharmacist 206 may be provided with an education and risk management tutorial or other training program for filling or otherwise providing the drug or product.

In block 308, the enrollment & validation engine 108 may update one or more registries for the drug or product in the database 194 to include the enrolled patient/caregiver 202, physician 204, and/or pharmacy/pharmacist 206. According to an example embodiment of the invention, the database 194 may have a single registry for all of the enrolled patient/caregiver(s) 202, physician(s)/healthcare provider(s) 204, and/or pharmacy/pharmacist(s) 206. In another example embodiment of the invention, however, there may be respective patient/caregiver, physician, and pharmacy/pharmacist registries for each of respective enrolled patient/caregiver(s) 202, physician(s) 204, and/or pharmacy/pharmacist(s) 206.

The database 194 may also include a reporting database for storing any information associated with educational material deliveries. For example, the database 194 may store a date, time, and/or recipient, for each educational material that is provided to a patient/caregiver 202, physician 204, and/or pharmacy/pharmacist 206. Likewise, the database 194 may also store information associated with whether the patient/caregiver 202, physician 204, and pharmacy/pharmacist 206 has reviewed or acknowledged reviewing the received educational information in block 306. The acknowledgement may include the patient/caregiver(s) 202, physician(s) 204, and pharmacy/pharmacist 206 verbally indicating (or alternatively using a telephone keypad entry via an IVR system 209) to the call center 208 that the educational information has been received and/or understood. Likewise, the acknowledgment for a network portal/website 210 may include the selection of a button indicating that the educational information has been received and/or understood. Many other acknowledgments may be available, including those provided via email, facsimile, or postal mail. In an example embodiment of the invention, the acknowledgements may be required to complete the registration or enrollment process.

It will also be appreciated that upon a successful enrollment, the enrollment & validation engine 108 may assign an identifier for the enrolled patient/caregiver(s) 202, physician(s) 204, and/or pharmacy/pharmacist(s) 206. For example, the patient/caregiver 202 may be assigned a Patient ID. Likewise, the enrolled physician 204 may be assigned a Physician ID. Similarly, a pharmacist 206 may be assigned a Pharmacy ID. These assigned identifiers may be provided to the respective patient/caregiver(s) 202, physician(s) 204, and/or pharmacist(s) 206 via the call center 208, the network portal/website 210, or another communications means, including facsimile, email, postal mail, and the like. These assigned identifiers may also be stored in the database 194, perhaps in association with the registry entry for the enrolled patient/caregiver 202, physician 204, and/or pharmacy/pharmacist 206.

According to an example embodiment of the invention, the enrollments for the patient/caregiver(s) 202, physicians(s) 204, and/or pharmacy/pharmacist(s) 206 may be valid for only a certain period of time. Accordingly, the patient/caregiver(s) 202, physicians(s) 204, and/or pharmacy/pharmacist(s) 206 may need to be re-certified at regular intervals in order to maintain the validity of their enrollments, according to an example embodiment of the invention.

Figure 4:
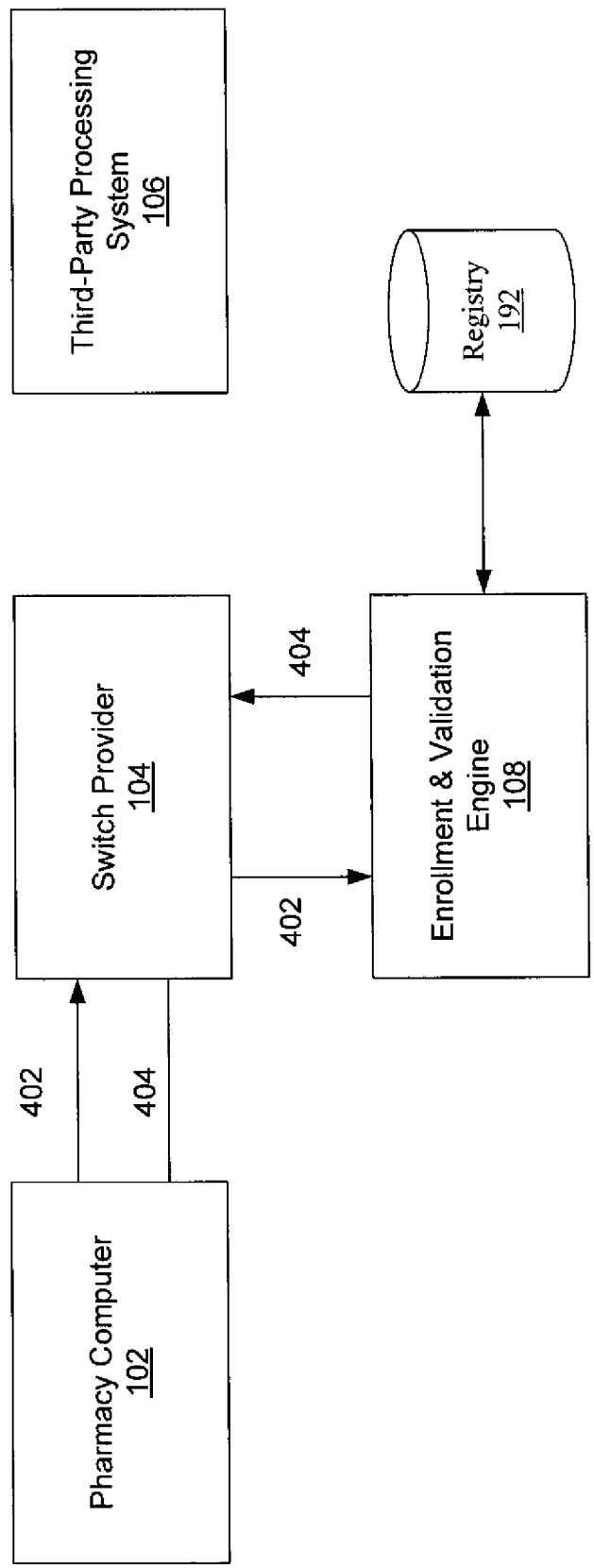
FIG. 4 illustrates an example system for processing eligibility verification requests for filling or refilling prescription drugs, according to an example embodiment of the invention.

FIG. 4 illustrates an example system for processing eligibility verification requests for filling or refilling prescription drugs, according to an example embodiment of the invention. The operation of the system of FIG. 4 will be discussed in conjunction with the flow diagram of FIG. 5.

Figure 5:
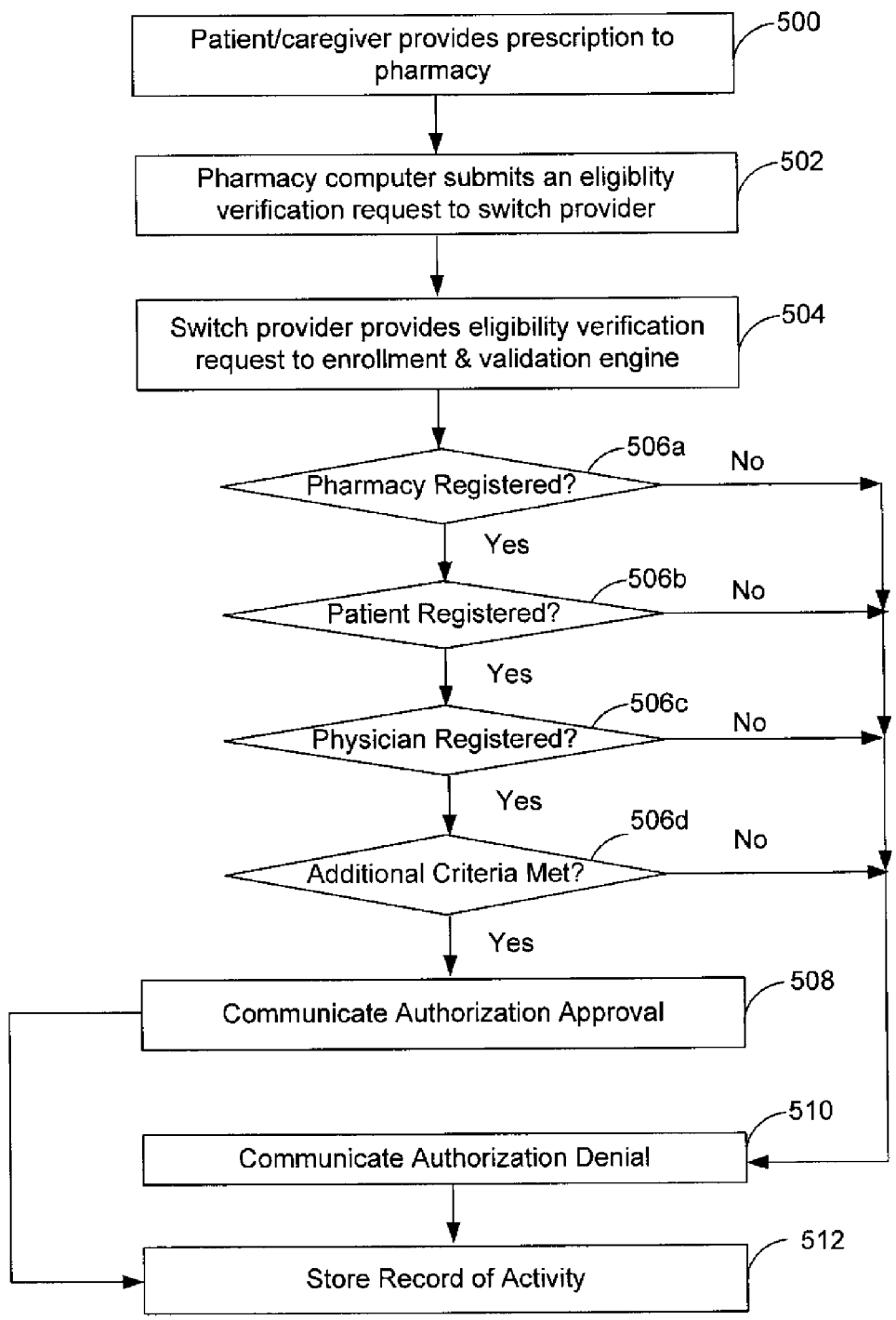
FIG. 5 illustrates an example flow diagram for processing eligibility verification requests for filling or refilling prescription drugs, according to an example embodiment of the invention.

Referring now to FIGS. 4 and 5, in block 500, a patient may visit a physician or other healthcare provider for diagnosis of a medical condition of the patient. The physician or other healthcare provider may prescribe a drug or product for the patient. The prescribed drug or product may be a highly regulated drug or product, according to an example embodiment of the invention. Accordingly, the prescription may be subject to eligibility verification in accordance with a Prescription Safety Network program, which may be indicated by a sticker affixed to a paper prescription, according to an embodiment of the invention. It will be appreciated that in an optional embodiment of the invention the physician or other healthcare provider may provide Medication Therapy Management (MTM) counseling (e.g., usage information) with the patient/caregiver. As part of the MTM counseling, the physician or other healthcare provider may complete an MTM counseling form, either manually via paper or electronically via web documentation tool, for delivery to the administrator of the Prescription Safety Network program (e.g., the enrollment & validation engine or an entity associated therewith), according to an example embodiment of the invention.

Still referring to block 500, the physician or other healthcare provider may also provide the patient/caregiver with instructions for registering with the Prescription Safety Network in accordance with an example embodiment of the invention. Once the patient/caregiver has registered with the Prescription Safety Network, as described herein, the patient/caregiver may provide a pharmacy with the prescription to be filled.

In block 502, the pharmacy computer 102 may transmit, communicate, or otherwise provide an eligibility verification request 402 or other authorization request to the switch provider 104. The eligibility verification request 402 may be a request associated with determining whether a drug or product prescribed for a patient by a physician or other healthcare provider can be filled by a pharmacy. The eligibility verification request 402 may include one or more of the following information:
- identification of the patient (or caregiver) that will be utilizing (or administering) the prescribed drug or product,
- identification of the pharmacy filling the prescribed drug or product,
- identification of the physician or other healthcare provider prescribing the drug or product, and/or
- a Banking Identification Number (BIN)/Processor Control Number (PCN).

According to an example embodiment of the invention, the eligibility verification request 402 may be associated with a standard NCPDP (National Council for Prescription Drug Programs) eligibility verification transaction. With a standard NDPDP eligibility verification transaction, an identification of the drug or product may be determined or otherwise implied based upon the BIN/PCN of the eligibility verification request 402. By way of example, different drugs may be assigned to different BIN/PCN's. According to an alternative embodiment of the invention, an eligibility verification request 402 may explicitly provide an identification of the drug or product, perhaps using an NDC number. It will be appreciated that many variations of the eligibility verification request may be available without departing from example embodiments of the invention.

In block 504, the switch provider 104 may receive the eligibility verification request 402. The switch provider 104 may then deliver the eligibility verification request 402 to the enrollment & validation engine 108. Where the switch provider 104 and the enrollment & validation engine 108 are the same entity or processor-based system, the delivery of the eligibility verification request 402 may be an internal delivery. On the other hand, where the switch provider 104 and enrollment & validation engine 108 are distinct entities or processor-based systems, then the delivery of the eligibility verification request 402 may be an external delivery across one or more networks, such as network 110.

Blocks 506a-506d may then involve the enrollment & validation engine 108 validating the received eligibility verification request 402. The validation by the enrollment & validation engine 108 may include determining whether a drug or product prescribed for a patient by a physician or other healthcare provider can be filled by a pharmacy. More specifically, according to block 506a, the enrollment & validation engine 108 may utilize database 192 to determine whether the pharmacy identified by the request 402 is authorized to fill or refill the prescription for the requested drug or product. According to an example embodiment of the invention, the enrollment & validation engine 108 may determine whether the pharmacy has previously registered with the Prescription Safety Network for the drug or product to be prescribed. By way of example, the enrollment & validation engine 108 may determine whether the pharmacy identification of the request 402 can likewise be matched in a pharmacy/pharmacist registry for the requested drug or product in database 192.

If block 506a determines that the pharmacy is not authorized to fill or refill the prescription for the requested drug or product, then in block 510, then the enrollment & validation engine may provide a response 404 in the form of an authorization denial to the switch provider 104, which in turn may provide the response 404 to the pharmacy computer 102. The authorization denial may indicate that the pharmacy is not registered with the Prescription Safety Network. The pharmacy computer 102 may then present the authorization denial to the pharmacist or other pharmacy employee. An example of a message for an authorization denial is illustrated in FIG. 6A.

On the other hand, if block 506a determines that the pharmacy is authorized to fill or refill the prescription for the requested drug or product, then processing may proceed to block 506b. In block 506b, the enrollment & validation engine 108 may utilize the database 192 to determine whether the patient identified by the request 402 is authorized to utilize the prescribed drug or product. According to an example embodiment of the invention, the enrollment & validation engine 108 may determine whether the patient/caregiver has previously registered with the Prescription Safety Network for the prescribed drug or product. By way of example, the enrollment & validation engine 108 may determine whether the patient (or caregiver) identified by the request 402 can likewise be matched in a patient registry for the prescribed drug or product in database 192.

If block 506b determines that the patient is not authorized to utilize the prescribed drug or product, then in block 510, the enrollment & validation engine 108 may provide a response 404 in the form of an authorization denial to the switch provider 104, which in turn may provide the response 404 to the pharmacy computer 102. The authorization denial may indicate that the patient is not enrolled in the Prescription Safety Network program. On the other hand, if block 506*b* determines that the patient is authorized to utilize the prescribed drug or product, then processing may proceed to block 506*c*. In block 506*c*, the enrollment & validation engine 108 may utilize the database 192 to determine whether the physician or other healthcare provider identified by the request 402 is authorized to prescribe the requested drug or product. According to an example embodiment of the invention, the enrollment & validation engine 108 may determine whether the prescribing physician or other healthcare provider has previously registered with the Prescription Safety Network program for the prescribed drug or product. By way of example, the enrollment & validation engine 108 may determine whether the patient identified by the request 402 can likewise be matched in a patient registry for the prescribed drug or product in database 192.

If block 506*c* determines that the physician or other healthcare provider is not authorized to prescribe the requested drug or product, then in block 510, the enrollment & validation engine may provide a response 404 in the form of an authorization denial to the switch provider 104, which in turn may provide the response 404 to the pharmacy computer 102. The authorization denial may indicate that physician is not enrolled in the Prescription Safety Network program. On the other hand, if block 506*c* determines that the physician or other healthcare provider is indeed authorized to prescribe the requested drug or product, then processing proceeds to block 506*d*.

In block 506*d*, any additional criteria required for filling the prescription may be verified. As an example, the enrollment & validation engine 108 may verify that the patient information, either received in the claim request information or retrieved from database 194 (e.g., age, weight, pregnancy status, conditions, other drugs, etc.), is compatible with manufacturer specifications for the requested drug or product. According to an example embodiment of the invention, a manufacturer specification for the drug or product may specify a minimum or maximum age for the drug or product, that a patient not be pregnant when taking the drug or product, that the drug or product should not be taken if certain other drugs and/or conditions are present (e.g., contraindications), and the like. Thus, the enrollment & validation engine 108 may check to determine that a patient is eligible to receive a requested drug or product based upon the information that may be received in the claim request information or retrieved from database 194 (e.g., age, weight, pregnancy status, conditions, other drugs, etc.). Likewise, block 506*d* may verify that the prescribed quantity for the drug or product does not exceed a maximum allowable amount for the patient (e.g., Quantity Dispensed, Days Supply, Quantity Dispensed/Days Supply ratio), according to an example embodiment of the invention. It will be appreciated that additional or alternative business rules may be implemented by the enrollment & validation engine 108 as necessary to provide controlled utilization, prescribing, and/or dispensing of the requested drug or product.

If the additional criteria in block 506*d* is not met, then in block 510, the enrollment & validation engine may provide a response 404 in the form of an authorization denial to the switch provider 104, which in turn may provide the response 404 to the pharmacy computer 102. The authorization denial may specify which of the additional criteria was not satisfied. On the other hand if the criteria in block 506*d* is indeed met, then processing proceeds to block 508. In block 508, the enrollment & validation may provide a response 404 in the form of an authorization approval to the switch provider 104, which in turn may provide the response 404 to the pharmacy computer 102. The pharmacy computer 102 may then present the authorization approval to the pharmacist or other pharmacy employee. The authorization approval may include an Authorization ID, according to an example embodiment of the invention. An example of a message for an authorization approval is illustrated in FIG. 6B.

According to an embodiment of the invention, the authorization approval may also be accompanied with a M™ counseling notification. The MTM counseling notification may require the pharmacy/pharmacist to perform MTM counseling with the patient/caregiver for the provided drug or product. As part of the MTM counseling, the pharmacy/pharmacist may complete an MTM counseling form, either manually via paper or electronically via web documentation tool, for delivery to the administrator of the Prescription Safety Network program (e.g., the enrollment & validation engine or an entity associated therewith), according to an example embodiment of the invention.

In block 512, the enrollment & validation engine 108 may store reporting information in the database 194. According to an example embodiment of the invention, the reporting information may include logs of authorization approvals and/or denials, including a record of the requested drug or product, the Authorization ID or the reason(s) for the denial, and/or associated date/time information. The use of the logs may allow for further analysis of compliance with a Prescription Safety Network program sponsored by the enrollment & validation engine 108 for a particular drug or product.

It will be appreciated that many variations of FIGS. 4 and 5 are available without departing from example embodiments of the invention. As an example, one or more of blocks 506*a-d* may be optional. By way of an example, only some of the patients, physicians or other healthcare providers, and/or pharmacies/pharmacists may need to be enrolled with the enrollment & validation engine 108 for the Prescription Safety Network program. For example, prescribed drugs with very high risks may require that all of the patient/caregiver, physician or other healthcare provider, and pharmacy/pharmacist involved with utilizing, prescribing, or dispensing the requested drug or product may need to be enrolled. On the other hand, for drugs with lesser risks, perhaps only one or two of the patient/caregiver, physician or other healthcare provider, and/or pharmacy/pharmacist may need to be enrolled.

According to another variation of FIGS. 4 and 5, a pharmacy computer 102 may also submit an eligibility verification request to the enrollment & validation engine 108 via an Internet/web portal site. The Internet/web portal site may include one or more fields for receiving an identification of the patient (or caregiver) that will be utilizing (or administering) the prescribed drug or product, identification of the pharmacy filling the prescribed drug or product, and identification of the physician or other healthcare provider prescribing the drug or product. The enrollment & validation engine 108 may then perform the processing described in blocks 506*a-d*, and return an authorization approval or denial. The authorization approval or denial may be presented by the Internet/web portal site, according to an example embodiment of the invention.

Figure 7:
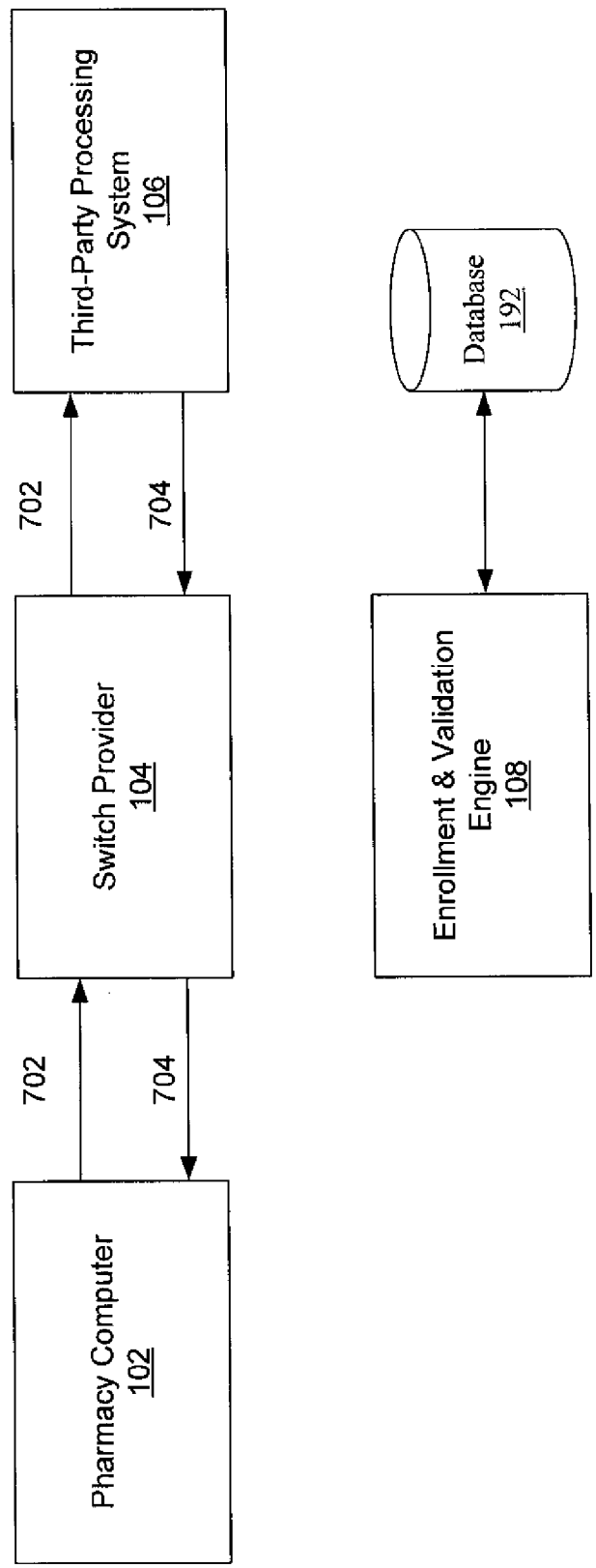
FIG. 7 illustrates an example block diagram for a prescription claim transaction, according to an example embodiment of the invention.

Once the pharmacy receives an authorization approval for filling the prescription, the pharmacy may proceed with billing, dispensing, counseling and/or collecting payment for the prescription drug or product. For a cash customer, the payment process may include collecting payment (e.g., credit/debit cards, check, actual cash, etc.) at the pharmacy's point of sale from the customer (e.g., patient/caregiver). However, an additional prescription claim transaction may be required for customers that may have coverage with a discount program, an insurance company, a PBM, and the like. FIG. 7 illustrates a block diagram for a prescription claim transaction, according to an example embodiment of the invention. The operation of the block diagram of FIG. 7 will be discussed in conjunction with the flow diagram of FIG. 8.

Figure 8:
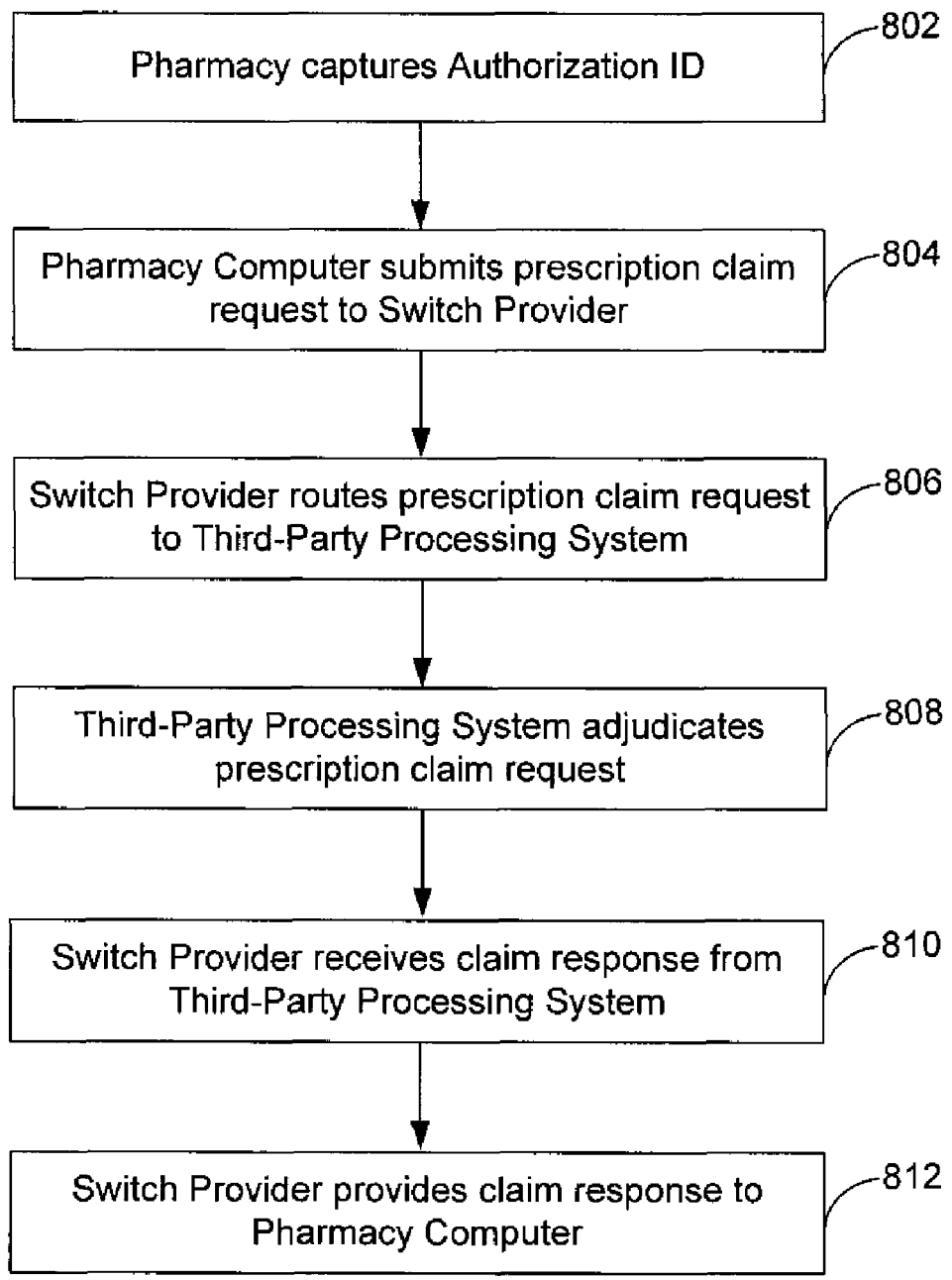
FIG. 8 illustrates an example flow diagram for a prescription claim transaction, according to an example embodiment of the invention.

Referring now to FIGS. 7 and 8, in block 802, the pharmacy captures the Authorization ID from the received authorization approval. In block 804, the pharmacy computer 102 may submit a prescription claim request 702 to the switch provider 104. In an example embodiment of the invention, the claim request 702 may include one or more of the following information:
- an identification of the drug or product (e.g., National Drug Code (NDC)) (and/or a condition or a disease),
- patient indication(s),
- a quantity and/or days supply of the drug or product,
- pricing information for the drug or product,
- a date of the claim request,
- a pharmacy identification number, or alternatively, other identification that is associated with pharmacy/pharmacist 206 enrollment with the enrollment & validation engine 108,
- a patient identification number other identification that is associated with patient/caregiver 202 enrollment with the enrollment & validation engine 108,
- a physician identification number or other identification that is associated with physician 204 enrollment with the enrollment & validation engine 108, and/or
- Authorization ID from the received authorization approval.

It will be appreciated that while some example information has been illustrated for the example claim request, alternate or additional information may also be included without departing from example embodiments of the invention. For example, the prescription claim request 702 may further include additional patient information, such as a date of birth for the patient or a Gender Code for the patient. The claim request may also include a Banking Identification Number (BIN)/Processor Control Number (PCN) for identifying a third-party processing system 106 as a destination of the claim request.

In block 806, the switch provider 104 may receive the prescription claim request 702. The prescription claim request 702 may be then provided or routed from the switch provider 104 to the third-party processing system 106 for coverage or benefits determination by a discount program, insurance company, PBM, government payor, etc. In block 808, the third-party processing system 106 may adjudicate the prescription claim request 702 and generate a claim response 704. The claim response 704 may specify the covered amount and the patient-responsible amount (e.g., a copay amount). The third-party processing system 106 may then provide the claim response 704 to the switch provider 108, as illustrated in block 810. The switch provider 104 may then route or otherwise communicate the claim response 104 to the pharmacy computer 102. The patient is the responsible for the patient-responsible amount at the pharmacy's point of sale. The pharmacist may then dispense or otherwise provide the requested drug or product to the patient/caregiver.

It will be appreciated that variations of FIG. 8 are available without departing from example embodiments of the invention. For example, in FIG. 8, the switch provider 104 may operate in conjunction with the enrollment & validation engine 108 to determine whether the Authorization ID received in the claim request 702 has been provided in accordance with previous validation of the eligibility verification request. If the Authorization ID is valid, the claim request 702 may be routed by the switch provider 104 to the third-party processing system 106 for adjudication. On the other hand, if the Authorization ID is not valid, then a message may be provided to the pharmacy computer 102 indicating an invalid Authorization ID, and requesting either resubmission of the claim request 702 with a valid Authorization ID.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A method for a prescription safety network program, comprising:
   receiving, by at least one provider computer from a pharmacy computer, an eligibility verification request for a prescribed drug, wherein the eligibility verification request includes a pharmacy identifier, a patient identifier, and a physician identifier;
   determining, by the at least one provider computer based upon comparing the received pharmacy identifier to stored information associated with pharmacies having one of (i) a Drug Enforcement Agency (DEA) number, (ii) a National Provider Identifier (NPI), or (iii) a state license that permits dispensing the prescribed drug, that a requesting pharmacy associated with the pharmacy identifier is authorized for filling the prescribed drug;
   determining, by the at least one provider computer based upon the received patient identifier, that a patient associated with the patient identifier is authorized for utilizing the prescribed drug;
   determining, by the at least one provider computer based upon the received physician identifier, that a physician associated with the physician identifier is authorized for prescribing the prescribed drug;
   generating based on a positive determination that the requesting pharmacy is authorized to fill the prescribed drug, the patient is authorized to utilize the prescribed drug, and the physician is authorized to prescribe the prescribed drug, an approval authorization by the at least one provider computer, the approval authorization comprising an authorization ID;
   delivering, by the at least one provider computer, the generated approval authorization to the pharmacy computer in response to the eligibility verification request, wherein the approval authorization permits the pharmacy to submit a prescription claim request requesting payment for the prescribed drug;
   subsequent to delivering the approval authorization, receiving, by the at least one provider computer from the pharmacy computer, the prescription claim request for the prescribed drug, the prescription claim request comprising a received authorization ID;
   evaluating the received authorization ID to determine if the received authorization ID matches the authorization ID delivered with the approval authorization;
   delivering the prescription claim request from the at least one provider computer to a third-party processing system for payment adjudication based on positive determination that the received authorization ID matches the authorization ID delivered with the approval authorization receiving an adjudicated claim response at the at least one provider computer from the third-party processing system; and delivering, by the at least one provider computer, the adjudicated claim response to the pharmacy computer in response to the prescription claim request, wherein the delivery of the approval authorization and the adjudicated claim response permits the pharmacy to dispense the prescribed drug to the patient.

2. The method of claim 1, wherein one or more of the pharmacy, patient, and physician enrolls with the prescription safety network program via a call center, interactive voice response system, or Internet website/portal prior to being authorized for filling, utilizing, or prescribing the prescribed drug.

3. The method of claim 2, wherein in association with enrollment with the prescription safety network program, one or more of the pharmacy, patient, and physician receive educational information relating to the prescribed drug.

4. The method of claim 3, wherein the educational information includes medication guides or safety guides for the prescribed drug.

5. The method of claim 1, wherein prior to delivering the approval authorization, the method further includes determining, by the at least one provider computer, that information of the patient is compliant with manufacturer or safety specifications for the prescribed drug.

6. The method of claim 1, wherein the eligibility verification request is associated with a standard National Council for Prescription Drug Programs (NCPDP) eligibility verification transaction, and further comprising:

identifying, by the at least one provider computer based upon a Banking Identification Number (BIN)/Processor Control Number (PCN) included in the eligibility verification request, the prescribed drug.

7. The method of claim 1, wherein if the received authorization ID does not match the authorization ID delivered with the approval authorization, then the prescription claim request is processed by delivering a message from the at least one provider computer to the pharmacy computer, the message comprising an indication that the received authorization ID is invalid.

8. The method of claim 7, wherein the adjudication by the third-party processing system results in a determination of a patient-responsible amount payable by the patient when the pharmacy dispenses the prescribed drug to the patient.

9. The method of claim 1, further comprising the step of:
based on a determination that at least one of the requesting pharmacy, the patient, and the physician are not enrolled with the prescription safety network program, generating and transmitting a denial of authorization from the provider computer to the pharmacy computer.

10. The method of claim 9, wherein the denial of authorization prevents the pharmacy from providing the prescribed drug to the patient by disallowing a request for payment by the pharmacy for the prescribed drug.

11. A system for a prescription safety network program, comprising:
a memory for storing computer-executable instructions;
a processor in communication with the memory, wherein the processor is configured to execute the computer-executable instructions to:
receive, from a pharmacy computer, an eligibility verification request for a prescribed drug, wherein the eligibility verification request includes a pharmacy identifier, a patient identifier, and a physician identifier;

determine, based upon comparing the received pharmacy identifier to stored information associated with pharmacies having one of (i) a Drug Enforcement Agency (DEA) number, (ii) a National Provider Identifier (NPI), or (iii) a state license that permits dispensing the prescribed drug, that a requesting pharmacy associated with the pharmacy identifier is authorized for filling the prescribed drug;

determine, based upon the received patient identifier, that a patient associated with the patient identifier is authorized for utilizing the prescribed drug;

determine, based upon the received physician identifier, that a physician associated with the physician identifier is authorized for prescribing the prescribed drug;

generate, based upon a positive determination that the requesting pharmacy is authorized to fill the prescribed drug, the patient is authorized to utilize the prescribed drug, and the physician is authorized to prescribe the prescribed drug, an approval authorization comprising an authorization ID;

direct communication of the generated approval authorization to the pharmacy computer in response to the eligibility verification request, wherein the approval authorization permits the pharmacy to submit a prescription claim request requesting payment for the prescribed drug;

subsequent to directing communication of the generated approval authorization, receive, from the pharmacy computer, the prescription claim request for the prescribed drug, the prescription claim request comprising a received authorization ID;

evaluate the received authorization ID to determine if the received authorization ID matches the authorization ID of the approval authorization;

direct communication of the prescription claim request to a third-party processing system for payment adjudication based on a positive determination that the received authorization ID matches the authorization ID of the approval authorization;

receive an adjudicated claim response from the third-party processing system; and direct communication of the adjudicated claim response to the pharmacy computer in response to the prescription claim request, wherein the delivery of the approval authorization and the adjudicated claim response permits the pharmacy to dispense the prescribed drug to the patient.

12. The system of claim 11, wherein one or more of the pharmacy, patient, and physician enrolls with the prescription safety network program via a call center, interactive voice response system, or Internet website/portal prior to being authorized for filling, utilizing, or prescribing the prescribed drug.

13. The system of claim 12, wherein in association with enrollment with the prescription safety network program, one or more of the pharmacy, patient, and physician receive educational information relating to the prescribed drug.

14. The system of claim 13, wherein the educational information includes medication guides or safety guides for the prescribed drug.

15. The system of claim 11, wherein prior to delivering the approval authorization, the processor is further configured to execute the computer-executable instructions to determine that information of the patient is compliant with manufacturer or safety specifications for the prescribed drug.

16. The system of claim 11, wherein the eligibility verification request is associated with a standard National Council for Prescription Drug Programs (NCPDP) eligibility verification transaction, and wherein the processor is further configured to evaluate a Banking Identification Number (BIN)/Processor Control Number (PCN) included in the eligibility verification request to determine the prescribed drug.

17. The system of claim 11, wherein if the received authorization ID-does not match the authorization ID delivered with the approval authorization, then the prescription claim request is processed by delivering a message from the at least one provider computer to the pharmacy computer, the message comprising an indication that the received authorization ID is invalid.

18. The system of claim 17, wherein the adjudication by the third-party processing system results in a determination of a patient-responsible amount payable by the patient when the pharmacy dispenses the prescribed drug to the patient.

19. The system of claim 11, wherein the processor is further configured to execute the computer-executable instructions to:
    based on a determination that at least one of the requesting pharmacy, the patient, and the physician are not enrolled with the prescription safety network program, generate a denial of authorization and direct communication of the denial of authorization to the pharmacy computer.

20. The system of claim 19, wherein the denial of authorization prevents the pharmacy from providing the prescribed drug to the patient by disallowing a request for payment by the pharmacy for the prescribed drug.

\* \* \* \* \*